United States Patent [19]

Plaia et al.

[11] Patent Number: 5,084,010
[45] Date of Patent: Jan. 28, 1992

[54] SYSTEM AND METHOD FOR CATHETER CONSTRUCTION

[75] Inventors: Mark Plaia, Redwood City; Richard L. Mueller, Mountain View; Chris Decaria, Los Altos, all of Calif.

[73] Assignee: Devices For Vascular Intervention, Inc., Redwood City, Calif.

[21] Appl. No.: 482,421

[22] Filed: Feb. 20, 1990

[51] Int. Cl.⁵ .............................................. A61B 17/22
[52] U.S. Cl. ........................................ 604/22; 606/159; 606/194
[58] Field of Search ............... 606/159, 170, 171, 205, 606/194; 604/22

[56] References Cited

U.S. PATENT DOCUMENTS

| | | | |
|---|---|---|---|
| 3,173,414 | 3/1965 | Guillant | 606/171 X |
| 3,336,927 | 8/1967 | Klebanoff | 606/159 |
| 3,433,226 | 3/1969 | Boyd | 606/159 |
| 3,565,062 | 2/1971 | Kuris | 606/159 |
| 4,494,549 | 1/1985 | Namba et al. | |
| 4,669,469 | 6/1987 | Gifford, III et al. | |
| 4,781,186 | 11/1988 | Simpson et al. | 606/171 |
| 4,819,634 | 4/1989 | Shiber | 606/159 |
| 4,846,192 | 7/1989 | MacDonald | 604/22 |
| 4,857,045 | 8/1989 | Rydell | 606/159 X |
| 4,869,715 | 9/1989 | Sherburne | 604/22 |
| 4,926,858 | 5/1990 | Gifford, III et al. | |

FOREIGN PATENT DOCUMENTS 0163502  12/1985  European Pat. Off. .

Primary Examiner—Michael H. Thaler
Attorney, Agent, or Firm—Townsend and Townsend

[57] ABSTRACT

A catheter system comprises a flexible catheter tube or body having a housing secured to its distal end. A plurality of structurally distinct terminal components are provided to attach to the forward end of the housing, while a plurality of interchangeable interventional elements are provided to attach to a drive member within the catheter. By properly selecting the terminal components and the interventional elements, a wide variety of specific therapeutic and diagnostic capabilities may be provided.

22 Claims, 4 Drawing Sheets

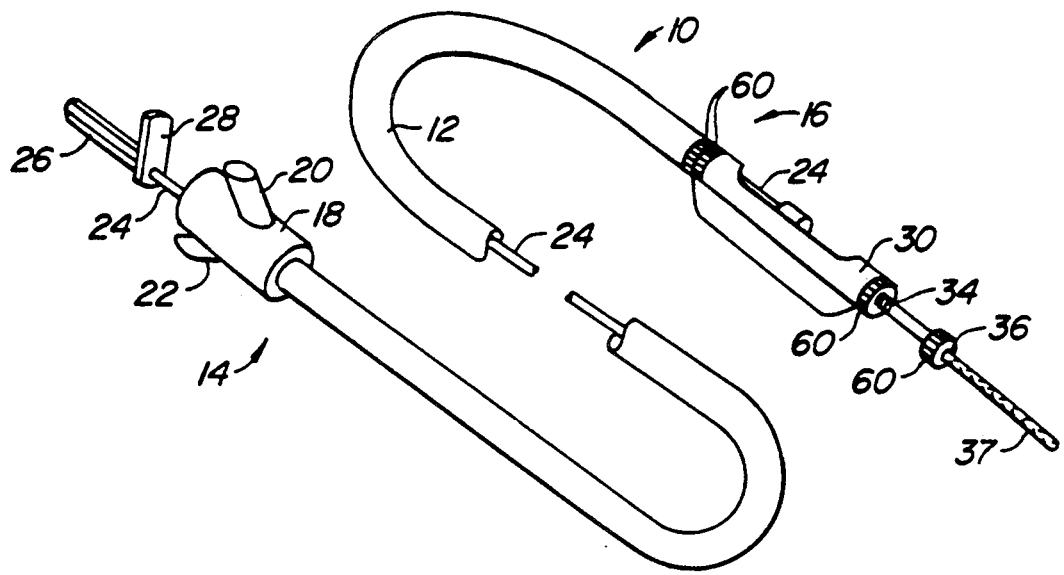
FIG._1.
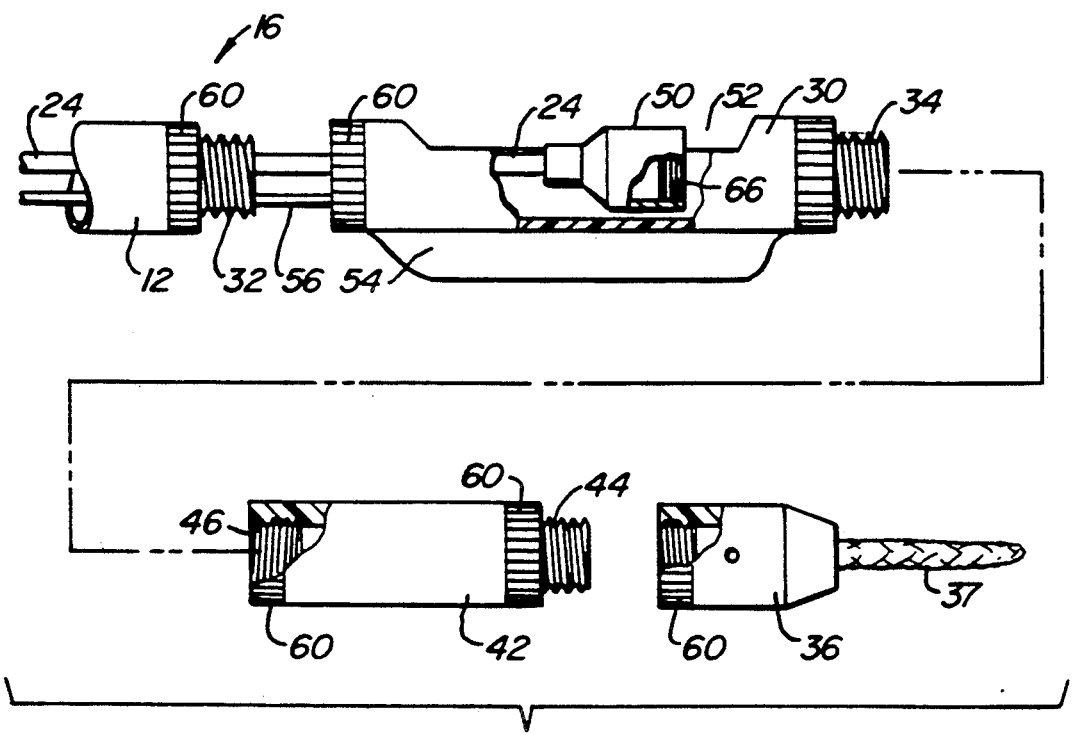
FIG._2.

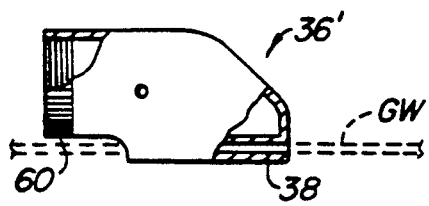
FIG._3A.
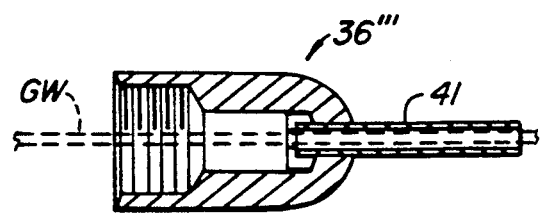
FIG._3C.
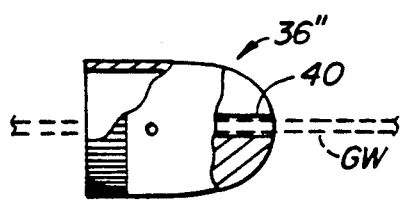
FIG._3B.
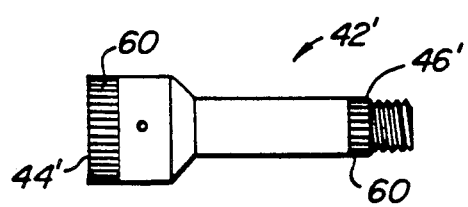
FIG._4A.
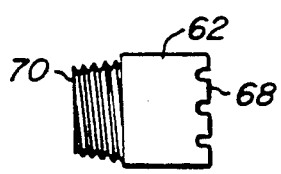
FIG._5A.
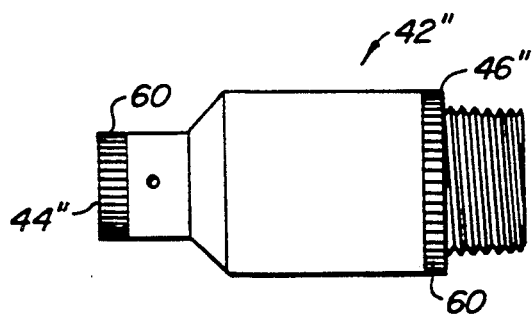
FIG._4B.
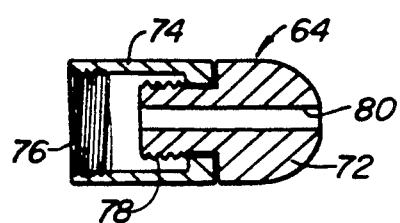
FIG._5B.
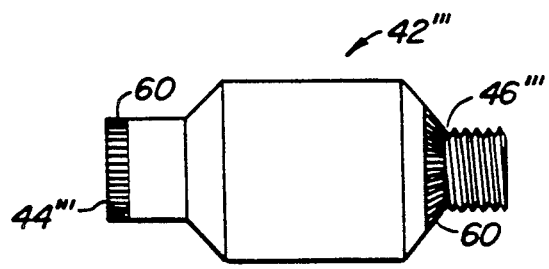
FIG._4C.

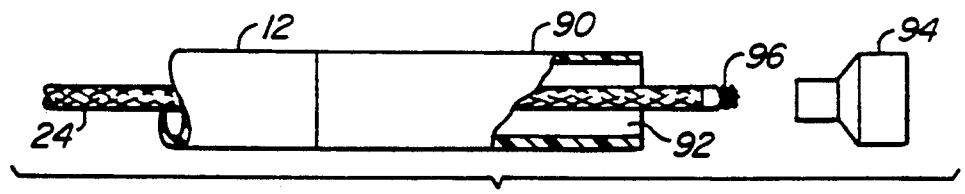
FIG._6.
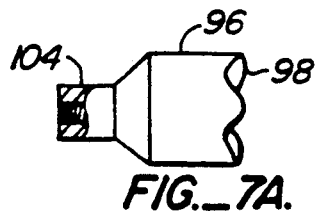
FIG._7A.
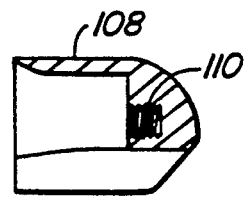
FIG._7C.
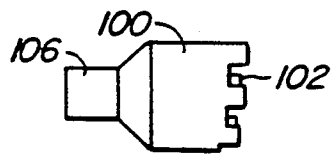
FIG._7B.
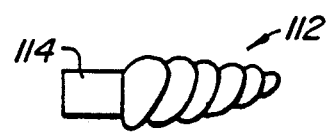
FIG._7D.
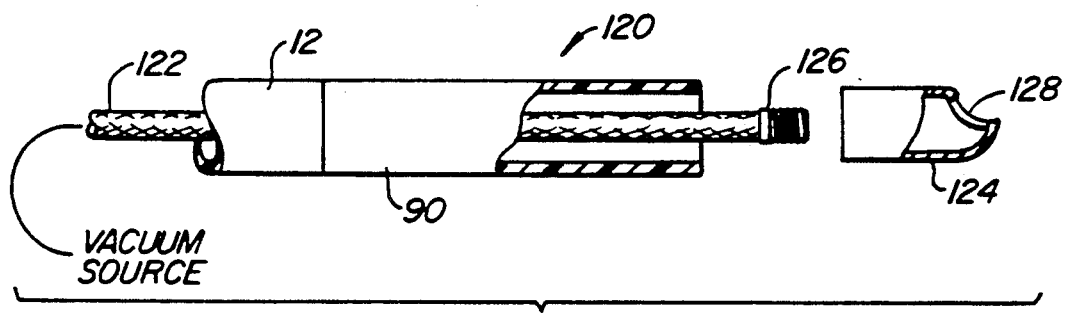
FIG._8.
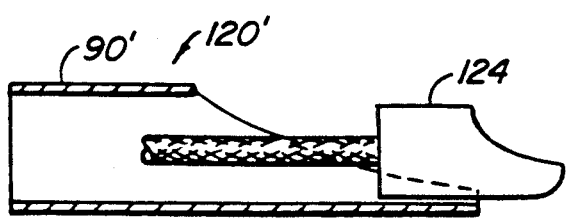
FIG._8A.
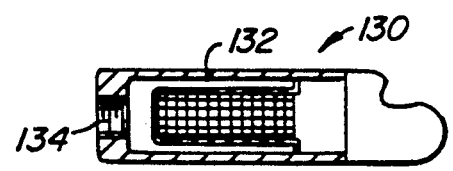
FIG._9.

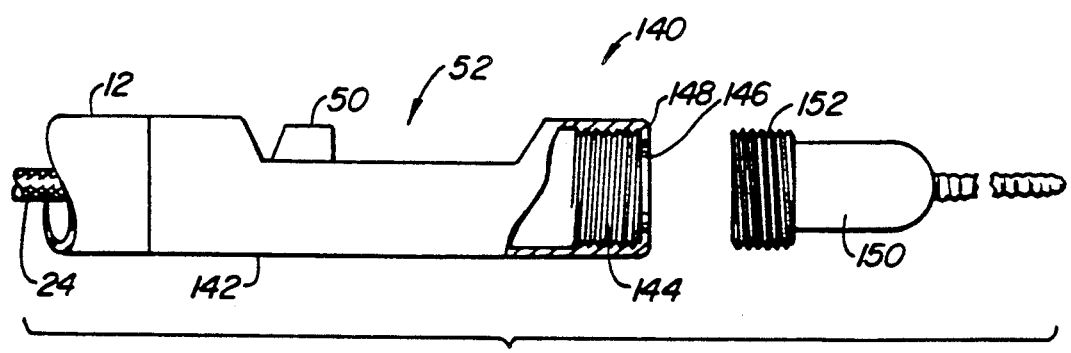
FIG._10.
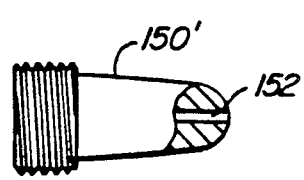
FIG._11A.
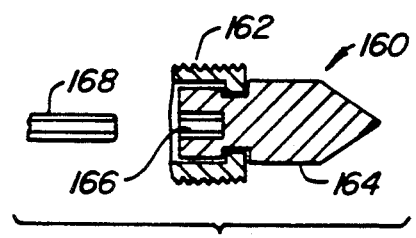
FIG._11B.
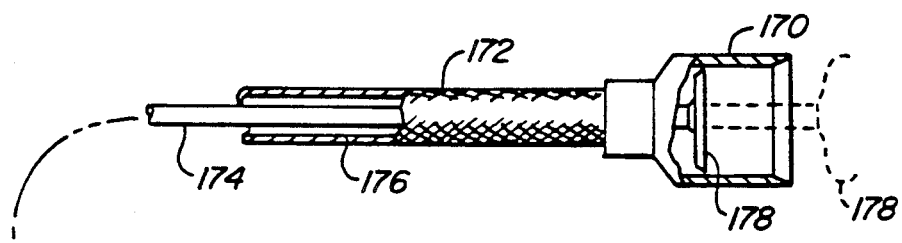
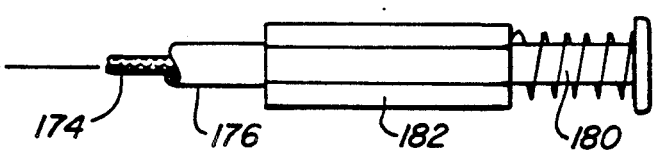
FIG._12.
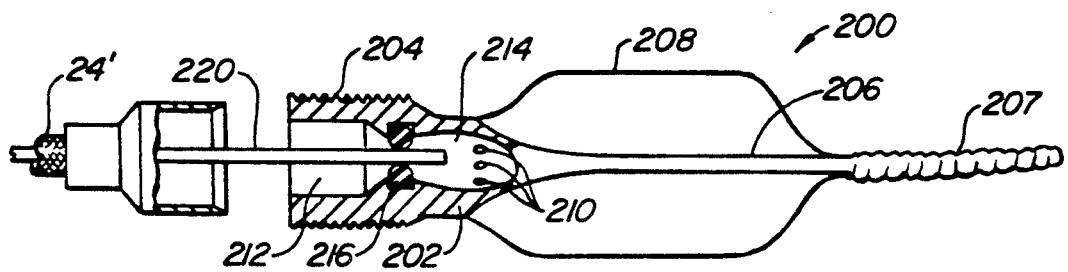
FIG._13.

SYSTEM AND METHOD FOR CATHETER CONSTRUCTION

BACKGROUND OF THE INVENTION

1. Field of the Invention

The present invention relates generally to the construction and use of medical catheters. More particularly, the invention relates to an intravascular catheter system having a plurality of interchangeable components which allow a treating physician to modify the catheter assembly based on the condition of a particular patient.

Arteriosclerosis, also known as atherosclerosis, is a common human ailment arising from the deposition of fatty-like substances, referred to as atheroma or plaque, on the walls of blood vessels. Such deposits occur both in peripheral blood vessels that feed the limbs of the body and coronary blood vessels which feed the heart. When deposits accumulate in localized regions of a blood vessel, blood flow is restricted and the person's health is at serious risk.

Numerous approaches for reducing and removing such vascular deposits have been proposed, including balloon angioplasty where a balloon-tipped catheter is used to dilate a region of atheroma, atherectomy where a blade or other cutting element is used to sever and remove the atheroma, and laser angioplasty where laser energy is used to ablate at least a portion of the atheroma. In addition to such therapeutic approaches, a variety of techniques for transluminal imaging of atheroma and other diseased regions of the blood vessel have been proposed, including endoscopic imaging techniques and ultrasonic imaging techniques.

Even after a particular interventional approach has been selected, a particular catheter design incorporating the necessary therapeutic and/or diagnostic features must be chosen. Differences in patient anatomy, the location of the atheroma, the nature of the atheroma (particularly the degree of calcification), physician technique, and the like, can all dictate different configurations of the catheter.

For example, all types of vascular catheters generally employ a guide assembly which allows the physician to advance the catheter through the desired blood vessels. Such guide assemblies can comprise fixed guide wires or movable guide wires, where the movable guide wires may be received by central lumens (in an "over the wire" configuration) or an offset lumen (in a "monorail" configuration). For particular applications, each type of guide assembly may be further matched with one, two, three, or more, additional features, resulting in a very large number of potential configurations.

In the case of atherectomy catheters, choices exist between the type of cutting element employed, the type of collection chamber utilized for retaining the severed atheroma, as well as additional specific features which may be desirable for particular therapeutic techniques. A similar array of specific features exists for each of the laser, balloon, and imaging catheter systems.

In order to afford the necessary selection of features, physicians and hospitals have heretofore had to maintain very large inventories of catheters to provide the various combinations which a patient might require. It has been necessary to maintain the inventory at the hospital since the conditions observed during a therapeutic procedure may indicate the use of a different catheter. Maintenance of such large inventories of catheters can be very expensive, and it may in fact be impossible to maintain as large an inventory as would be desirable. In the latter case, a physician might have to compromise the selection of catheter when confronted with a condition which was unknown at the outset of the procedure.

It would therefore be desirable to provide catheter systems which can be configured to include a variety of specific features and capabilities and which allow the treating physician to modify the catheter construction as needed at the outset and during the course of a therapeutic and/or diagnostic procedure. Such a catheter system would both reduce the inventory of catheters which must be maintained by the physician or the hospital and would enhance the availability of catheters tailored to meet specific therapeutic and imaging needs. It would be particularly desirable to provide atherectomy catheter systems having the capability of selecting among different types of guide assemblies, collection chambers, cutting elements, and other features as described in more detail hereinafter.

2. Description of the Background Art

European Patent Application 163 502 and U.S. Pat. No. 4,669,469, the disclosures of which are incorporated herein by reference, each describe an atherectomy catheter comprising a distal housing having an axially translatable blade therein. The blade may be moved past a side opening in the housing to sever adjacent atheroma in a blood vessel. Copending application Ser. No. 07/312,108, now U.S. Pat. No. 5,047,040 the disclosure of which is incorporated herein by reference, describes an atherectomy catheter comprising a distal housing or collection chamber having an axially translatable blade, where the blade may be extended forwardly of the housing to sever atheroma. The housing is illustrated to be screwed onto a fitting on the catheter tube, but no suggestion is made that different housings may be substituted. Copending applications having Ser. Nos. 07/045,916abandoned; 07/117,072abandoned ; and 07/298,846now U.S. Pat. No. 4,979,951 , each of which is incorporated herein by reference, describe atherectomy catheters having non-interchangeable functional components corresponding generally to certain of the interchangeable functional components of the present invention. U.S. Pat. No. 4,494,549, discloses a combined optical and ultrasonic endoscope having a detachable ultrasonic scanner which may be replaced by a cover 33.

SUMMARY OF THE INVENTION

According to the present invention, catheter systems are provided with interchangeable components which are structurally and functionally distinct so that different catheter configurations may be constructed by a treating physician immediately before and/or during therapeutic and diagnostic catheter procedures. The catheter systems include a flexible tube having proximal and distal ends and an open-ended cylindrical housing which is secured to the distal end of the flexible tube. Optionally, the cylindrical housing may be detachably secured to the flexible tube.

In a first embodiment of the present invention, the catheter system further includes a plurality of structurally and functionally distinct terminal components which are capable of interchangeably attaching to the distal end of the cylindrical housing. Generally, the different components will serve different functions which may be from time to time required during the therapeutic catheter procedure. In particular, in the case of vascular catheters, the terminal components may be compatible with different guide wire systems, including over-the-wire systems, monorail systems, fixed guide wire systems, over-the-wire spring tips, and the like. Alternatively, terminal components may comprise a rotatable nose cone which can be utilized to facilitate passage of the catheter through vascular constrictions.

In a second embodiment of the present invention, the catheter system further includes a drive member extending within the flexible tube from its proximal end to the housing. The drive member is capable of both rotational movement and axial translation relative to the housing and includes a means for detachably securing an interventional element to its distal end. A plurality of structurally and functionally distinct interventional elements are provided so that a treating physician can choose the element best suited for the patient's particular condition. For example, a variety of cutting elements may be utilized, with the particular cutting element chosen depending on the hardness of the atheroma. For hardened or calcified atheroma, a cutter having a serrated blade may be used. For very soft atheroma, a vacuum element may be utilized for aspirating the atheroma material into the catheter. In the latter case, the drive member of the catheter system will be capable of providing a vacuum to the vacuum element. In general, the interventional elements may be utilized by extending them forward through the open end of the cylindrical housing or by moving the element past the aperture formed on the side of the cylindrical housing. Other interventional or diagnostic elements, such as ultrasonic transducers may also find use.

With both of the above embodiments, it is desirable to prevent detachment and separation of the components while the catheter is in use. The present invention allows the treating physician to visually observe the status of the catheter while it is being inserted into the patient. In particular, radiopaque bands are formed on adjacent components which comprise the catheter, and the bands will be fluoroscopically observed by the treating physician. So long as the detachable component remains firmly secured to the remaining components, the bands will remain together, usually appearing as a single band under the fluoroscope. As soon as a detachable component begins to separate, however, the single band initially observed will separate into two distinct bands. Such separation alerts the physician that the catheter should be removed immediately in order to resecure or replace the detachable component.

A third embodiment of the catheter system of the present invention is provided which is unable to disassemble while in use, even if the detachable component has completely separated from the remaining components of the catheter. In the third embodiment, the cylindrical housing has an aperture formed on one side thereof. The open end of the housing is internally threaded and terminates in a constriction having a preselected diameter. A detachable terminal component having external threads at a proximal end thereof may then be inserted into the housing through the aperture and threaded into place. By properly sizing the constriction in the open end of the housing relative to the terminal component, loss of the terminal component through the open end of the housing can be avoided.

Using the catheter systems of the present invention, a treating physician may select a particular terminal component and/or interventional element based on the patient's condition. The selected component(s) may then be secured to the catheter and the catheter inserted into the patient by conventional means. By employing such interchangeable components, the inventory of catheters required at a single treatment facility may be greatly reduced. Moreover, should the physician encounter unexpected conditions or situations during a therapeutic catheter procedure, the catheter may be removed and reconfigured in order to best treat the newly-discovered condition.

BRIEF DESCRIPTION OF THE DRAWINGS

FIG. 1 is an isometric view of a vascular atherectomy catheter system constructed in accordance with the principles of the present invention.

FIG. 2 is a detailed view of the distal end of the catheter system of FIG. 1 with the components exploded to better illustrate their manner of attachment.

FIGS. 3A-3C illustrate alternative terminal components for the catheter system of FIGS. 1 and 2.

FIGS. 4A-4C illustrate alternative collection reservoirs components for the catheter system of FIGS. 1 and 2.

FIGS. 5A and 5B illustrate alternative interventional elements which may be attached to the cutting element of FIGS. 1 and 2, with the element of FIG. 5B also being attached to the cylindrical housing as a terminal component.

FIG. 6 illustrates an alternate configuration of the cylindrical housing of the present invention.

FIGS. 7A-7D illustrate alternate configurations for the interventional elements which may be attached to the drive member of the catheter system of FIG. 6.

FIGS. 8 and 8A illustrate alternate embodiments of the catheter system of the present invention employing a vacuum device as the interventional element.

FIG. 9 illustrates an alternative configuration for the vacuum device of FIG. 8.

FIG. 10 illustrates an alternate embodiment of the cylindrical housing of the catheter system of the present invention, wherein a terminal component is threadably attached to the interior of the distal end of the housing.

FIGS. 11A and 11B illustrate alternative terminal components for the embodiment of FIG. 10.

FIG. 12 illustrates a tamper mechanism which can be employed in certain of the cutting elements of the catheters of the present invention.

FIG. 13 illustrates a dilatation balloon assembly which may be attached as a terminal component to the distal end of the housing of FIG. 10.

DESCRIPTION OF THE SPECIFIC EMBODIMENTS

The specific embodiments described hereinafter all relate to the structure and use of atherectomy devices where particular components, such as terminal components and interventional components, may be interchangeably mounted on a catheter body. It will be appreciated, however, that the present invention is not limited to atherectomy devices but instead applies to virtually all types of intravascular catheters whenever the substitution of alternative terminal components or interventional components would be of benefit.

Referring now to FIGS. 1 and 2, an atherectomy catheter 10 includes a flexible catheter body or tube 12 which extends from a proximal end 14 to a distal end 16. A proximal housing 18 is secured to the proximal end of flexible tube 12 and includes an inflation port 20 and flushing port 22. A drive member 24, typically a torque cable as described in more detail hereinafter, extends from the proximal end of the housing 18 where it terminates in a coupling member 26 to the distal end 16 of flexible tube 12. A position lever 28 is also secured to the distal end of the drive member 24, with the coupling member 26 providing for rotation of the drive member (typically by attachment to a motorized drive unit as described in U.S. Pat. No. 4,771,774, the disclosure of which is incorporated herein by reference) and the position lever 28 allowing the user to axially translate the drive member within the flexible tube 12. As described thus far, the construction of catheter 10 is generally the same as that described in European Patent Application 163 502 and U.S. Pat. No. 4,669,469, both of which have been previously incorporated herein by reference.

A cylindrical housing 30 is secured to the distal end 16 of flexible tube 12 in such a way that the tube and housing together define a continuous internal lumen capable of receiving the drive member 24. The cylindrical housing 30 will typically be formed from a metal, such as stainless steel, but may also be formed from flexible materials such as organic polymers, e.g., polyurethane, or composites, e.g., fiber-impregnated polymers. As illustrated in FIG. 2, cylindrical housing 30 is attached to flexible tube 12 by a threaded fitting 32, allowing the housing to be removed and replaced with a structurally distinct interchangeable housing according to the present invention. The cylindrical housing 30, however, may also be fixedly attached to the flexible tube 12, typically by welding or adhesives, when it is not necessary to be able to replace the housing.

A threaded fitting 34 is provided at the forward or distal end of cylindrical housing 30 allowing attachment of an internally threaded terminal component 36 which is illustrated as having a fixed guide wire 37 at its forward or distal end. Alternative terminal components 36' and 36" are illustrated in FIGS. 3A and 3B, respectively. Terminal component 36' is also internally threaded so that it may be mounted on threaded fitting 34 in a manner similar to terminal component 36. Terminal component 36', however, includes a laterally-offset channel 38 which is able to receive a movable guide wire GW in a conventional manner (often referred to as a "monorail" configuration). Terminal component 36" is similar to terminal component 36', except that it includes a central channel 40 which is adapted to receive a guide wire GW which will extend down the central lumen of flexible tube 12 in a conventional manner (often referred to as an "over the guide wire" configuration).

The terminal component 36 may also include a hollow fixed over-the-wire spring tip of the type described in copending application Ser. No. 07/382,866, abandoned the disclosure of which is incorporated herein by reference. Referring to FIG. 3C, terminal component 36''' is similar to 36" except that it terminates in a fixed hollow spring tip 41 capable of receiving movable guide wire GW, as explained in said copending application.

Referring again to FIG. 2, a reservoir component 42 is optionally provided and includes a threaded fitting 44 and internally threaded end 46 which allows the reservoir component to be mounted between the cylindrical housing 30 and terminal component 36, 36' or 36". By utilizing the reservoir component 42, an additional volume for storing severed atheroma is provided, as will be described in more detail hereinafter.

Alternative configurations of the reservoir component are illustrated in FIGS. 4A–4C. Reservoir component 42' in FIG. 4A provides for a size reduction at the distal tip of catheter 10. Typically, the threaded proximal end 44' will have a diameter of 7 or 8 French (Fr), while the distal end 46' will have a diameter in the range from 6 to 7 Fr. The cylindrical housing 30 and terminal component 36 will, of course, be appropriately sized to mate with each end of the reservoir component 42'. Reservoir component 42" in FIG. 4B provides for a distal end having an increased diameter. Threaded proximal end 44" will have a diameter in the range from 7 to 8 Fr, while distal end 46" will have a diameter in the range from 8 to 9 Fr. Reservoir component 42''' does not alter the diameter of the distal end of the catheter 10, but rather provides an increased capacity in the central volume of the reservoir.

Referring again to FIG. 2, an interventional element 50 is secured to the distal end of drive member 24. In the illustrated embodiment, the interventional element 50 will be a circular cutting blade which may be fixedly or detachably secured to the drive member 24. Cylindrical housing 30 includes an elongate aperture 52 and an inflatable balloon 54 mounted on the housing in substantial opposition to the aperture 52. An inflation tube 56 is provided to connect the inflation port 20 on proximal housing 18 to the inflation balloon 54 on the cylindrical housing 30. The catheter 10 can thus be utilized in atherectomy procedures by introducing the catheter to the patient's vascular system, locating the cylindrical housing proximate a region of atheroma so that the aperture 52 lies adjacent said region, inflating the balloon 54 so that the atheroma enters the aperture, and simultaneously rotating and advancing cutting blade 50 to sever the atheroma and urge the atheroma forward into terminal component 36 and/or reservoir component 42. Such operation is described in greater detail in European Patent Application 163 502 and U.S. Pat. No. 4,669,469, previously incorporated herein by reference.

As the various components of catheter system 10 are detachable, it is important that separation and disassembly of the components while the catheter is introduced to the patient's vascular system be avoided. In the embodiment of FIGS. 1 and 2, this is accomplished by providing a radiopaque stripe 60 at each end of each component so that the strips on adjacent components will be brought together as the components are attached. This is best observed in FIG. 1, where stripe 60 at the distal end 16 of flexible tube 12 is positioned adjacent to a second stripe 60 at the proximal end of cylindrical housing 30. When viewed under fluoroscopic imaging equipment, the adjacent stripes 60 will appear to form a single stripe with no space. Should the adjacent components begin to separate, however, two distinct stripes will appear, allowing the treating physician to immediately observe the separation and immediately remove the catheter from the patient.

Referring now to FIGS. 5A and 5B, interventional components 62 and 64 may be secured within a forward threaded end 66 of the cutting blade 50. Interventional element 62 provides an alternate, serrated cutting edge 68 which is particularly useful with certain types of atheroma, particularly calcified atheroma. A threaded fitting 70 at the rear or proximal end of component 62 may simply be inserted into the threaded end 66 of the cutting blade 50.

Interventional element 64 of FIG. 5B is quite different. Element 64 includes a rotatable tip or "nose cone" 72 and a threaded shank 74, where tip 72 is able to rotate relative to shank 74. Threads 76 on shank 74 are adapted to mount on threaded fitting 34 of cylindrical housing 30, or alternatively on threaded fitting 44 of reservoir 42, while threads 78 on the rotatable tip 72 are able to threadably mate with the threads 66 on cutter 50. Note that the drawings are not to scale, and it will of course be necessary that threads 78 be dimensioned to pass through the interior of threaded end 34 on housing 30. In this way, the drive member 24 can be connected to the threaded tip 72 in order to allow for rotation. In place of a threaded connection, tip 72 may be frictionally coupled to the interior of cutter 50 in a conventional manner. Use of a rotatable tip 72 is particularly advantageous in passing the catheter 10 through relatively tight constrictions so that the aperture 52 may be brought adjacent to the atheroma. Usually, the forward surface of the tip 72 will be polished to facilitate passage through the constriction without damage to the blood vessel wall. An axially aligned channel 80 is provided in tip 72 so that the catheter 10 utilizing interventional element 64 may be introduced by a conventional over the guide wire technique.

Referring now to FIG. 6, a second cylindrical housing 90 having an open distal end 92 is illustrated. Housing 90 is shown to be fixedly attached to flexible tube 12, but detachable constructions could also find use. An interventional element 94 detachably mounts on a threaded fitting 96 at the distal end of drive member 24. As illustrated in FIG. 6, interventional element 94 is a circular cutter of the same type illustrated in FIGS. 1 and 2.

A variety of other interventional elements are illustrated in FIGS. 7A-7D. A cutting blade 96 having a serrated forward cutting edge 98 is illustrated in FIG. 7A, while a cutting blade having a castellated forward cutting edge 102 is illustrated in FIG. 7B. Both the elements 96 and 100 include threaded fittings 104 and 106, respectively, which mate with fitting 96 on drive member 24. A rearwardly oriented cutting blade 108 is illustrated in FIG. 7C, having an internal threaded cavity 110 for receiving fitting 96. A helical cutting blade 112 having a threaded fitting 114 is illustrated in FIG. 7D. Forward cutting atherectomy catheters of the type illustrated in FIG. 6 are generally described in copending application Ser. No. 07/312,108, which has previously been incorporated herein by reference.

Referring now to FIG. 8, a catheter system 120 having an open-ended cylindrical housing 90 mounted on the forward end of flexible tube 12 is illustrated. The catheter 120 construction is similar to that of FIG. 6, except that a hollow drive member 122 defining a vacuum lumen is connected to an aspiration element 124 at its distal end. A threaded fitting 126 is provided to connect to aspiration element 124 and also serves to provide a vacuum connection which can be connected to an external vacuum source through a proximal housing (not illustrated). As illustrated in FIG. 8, the forward end of housing 90 is square cut. The end may also be cut at an angle, as illustrated in FIG. 8A, to provide for enhanced directional capability.

Catheter system 120 is operated by extending the aspiration element 124 distally of cylindrical housing 90, contacting an opening 128 with the atheroma to be aspirated, and applying a vacuum to the aspiration element in order to draw the atheroma into the interior of the element.

An alternate aspiration element 130 is illustrated in FIG. 9. Element 130 includes an internal screen 132 which will entrap removed atheroma, preventing the atheroma from plugging the vacuum lumen of drive member 122. Threaded connection 134 is provided at the rear end of aspiration element 130 to mate with threaded connection 126 on the drive member 122.

Referring now to FIG. 10, a catheter system 140 having a cylindrical housing 142 mounted at the distal end of flexible tube 12 is illustrated. The construction of drive member 24 and cutting element 50 are similar to that described in connection with FIG. 1. Cylindrical housing 142, however, terminates in an internally threaded fitting 144 at its distal end. An opening 146 is provided in the distal end of housing 142 and is defined by a constriction or lip 148 having a preselected diameter. A terminal component 150, here illustrated to be a fixed guide wire component, includes a threaded shank 152 at its proximal end. The diameter of threaded proximal end 152 is selected to mate with terminal threads 144 in housing 140. The diameter of the threads 144 is sufficiently large, however, so that they cannot pass through opening 146 defined by lip 148. Thus, terminal component 150 can be mounted by inserting the terminal component through aperture 52 and threading the shank 152 into threads 144. The construction of FIG. 10 is particularly useful in that even if the terminal component 150 becomes unthreaded, it is not likely to be lost from the housing 140 as the shank 152 is unable to pass through opening 146.

Referring now to FIG. 11A, an alternate terminal component 150' adapted for over the wire insertion is illustrated. The terminal component 150' includes an axial channel 152 to receive a movable guide wire.

Referring now to FIG. 11B, a rotatable terminal component 160 adapted to be mounted in cylindrical housing 142 is illustrated. Threaded shank 162 which is received by threads 144 circumscribes a rotatable tip 164 having a hexagonal drive cavity 166. The distal end of tip 164 is illustrated as coming to a point, but will be appreciated that a variety of other configurations such as a blunt ball tip will also find use. Tip 164 may be driven by a hexagonal driver 168 which may be inserted through the flexible tube 12 or, optionally, through the hollow interior of drive member 24. Rotatable tip is useful for facilitating passage of the catheter through vascular constrictions, as described previously relative to FIG. 5B.

Referring now to FIG. 12, a particular configuration for a circular cutting element 170 is illustrated. The cutting element is mounted at the distal end of a hollow drive member 172. The attachment may be fixed or detachable. A second flexible element 174 extends in central lumen 176 of the drive member 172. A tamping plate 178 is secured to the distal end of member 174 and is secured to a plunger element 180 at its proximal end. The plunger 180 extends from a coupling member 182 which is similar to coupling member 26 in the embodiment of FIG. 1. By manually depressing plunger element 180, tamping member 178 may be extended to the position illustrated in broken line. Thus, atheroma material which is severed and gathered within the interior of cutting element 170 may be discharged. This is particularly useful in packing severed atheromic material into the forward end of side cutting catheters of the type illustrated in FIG. 1.

Referring now to FIG. 13, a dilatation balloon assembly 200 adapted to be mounted as a terminal component on cylindrical housing 142 of catheter 140 (FIG. 10) is illustrated. The assembly 200 includes a shaft member 202 having a threaded shank 204 at its proximate end and an elongate tubular portion 206 at its distal end. Usually, the shank 204 will be formed from a metal or hard plastic to facilitate threaded connection, while the tubular portion 206 will be formed from a flexible material, and the two segments may be joined by welding, adhesive bonding, or an equivalent procedure. A fixed guide wire 207 is secured to the distal end of the tubular portion 206 to allow positioning of the catheter within a patient's vascular system by conventional techniques. A dilatation balloon 208 is attached over the tubular portion 206, and a series of inflation ports 210 are provided to allow introduction of a suitable inflation medium, such as contrast medium or saline, as will now be described.

An interior region of threaded shank 204 is divided into a proximate chamber 212 and a distal chamber 214 by an O-ring 216. The O-ring 216 is sized to seal against an inflation tube 220 which may be introduced through a hollow drive member 24'. Once the inflation tube 220 is in place, the distal chamber 214 is isolated so that pressurized inflation medium will enter the balloon 208 through ports 210. In this way, balloon angioplasty interventional methods may be performed in conjunction with atherectomy procedures without the need to exchange catheters.

Although the foregoing invention has been described in detail for purposes of clarity of understanding, it will be obvious that certain modifications may be practiced within the scope of the appended claims.

What is claimed is:

1. A vascular catheter system comprising:
   a flexible tube having proximal and distal ends;
   a cylindrical housing secured to the distal end of the flexible tube and having an open distal end; and
   a plurality of structurally distinct terminal components having means for interchangeably attaching to the distal end of the cylindrical housing, wherein at least a distal region of the housing is radiopaque and at least a proximal region of each terminal component is radiopaque so that said radiopaque regions appear to be continuous when the terminal component is properly joined to the housing but apear to be separated when the terminal component has loosened but not separated from the housing.

2. A catheter system as in claim 1, further comprising a cylindrical extension which is threaded at one end to mate with the cylindrical housing and threaded at another end to mate with the terminal components.

3. A catheter system as in claim 1, wherein said radiopaque region of both the terminal component and the cylindrical housing is a radiopaque ring.

4. A catheter system as in claim 1, wherein the interchangeable terminal components are selected from the group consisting of an end piece having a fixed guide wire, and end piece having a central channel for receiving a movable guide wire, an end piece having an off-set channel for receiving a movable guide wire, an end piece having a rotatable tip, an end piece having a fixed hollow spring tip, and an end piece having a dilatation balloon.

5. A catheter system as in claim 1, wherein the cylindrical housing has an aperture formed on its side and the system further comprises:
   a drive member extending within the flexible tube from its proximal end to the housing, said drive member being capable of both rotation and axial translation relative to the housing;
   means for detachably securing an interventional element to a distal end of the drive member; and
   a plurality of structurally distinct interventional elements capable of attaching to said means for securing on the drive member.

6. A catheter system as in claim 5, wherein at least one of the interventional elements is a circular blade having an axially-extendible tamper element therein.

7. A catheter system as in claim 1, wherein the cylindrical housing is detachably secured to the flexible tube.

8. A catheter system as in claim 7, further comprising at least one additional cylindrical housing which is structurally distinct from the first cylindrical housing and which may be interchangeably secured to the flexible tube.

9. A catheter system comprising:
   a flexible tube having proximal and distal ends;
   a cylindrical housing secured to the distal end of the flexible tube and having an open distal end;
   a drive member extending within the flexible tube from its proximal end to the housing, said drive member being capable of both rotation and axial translation relative to said housing;
   means for detaching securing an interventional element to a distal end of the drive member; and
   a plurality of structurally distinct interventional elements capable of attaching to said means for securing on the drive member, whereby the interventional elements may be attached and removed from the drive member while the means for detachably securing is extended distally of the open distal end of the cylindrical housing; and
   a plurality of structurally distinct terminal components having means for interchangeably attaching to the open distal end of the cylindrical housing whereby the terminal component may be removed to allow the distal end of the drive member to be extended beyond the distal end of the housing and wherein at least a distal region of the housing is radiopaque and at least a proximal region of each terminal component is radiopaque so that said radiopaque regions appear to be continuous when the terminal component is properly joined to the housing but appear to be separated when the terminal component has loosened but not separated from the housing.

10. A catheter system as in claim 9, wherein the interventional element is an aspiration device and wherein the drive member is a hollow tube capable of coupling a vacuum source to the aspiration device.

11. A catheter system comprising:
   a flexible tube having proximal and distal ends;
   a cylindrical housing secured to the distal end of the flexible tube and having an open distal end;
   a drive member extending within the flexible tube from its proximal end to the housing, said drive member being capable of both rotation and axial translation relation to said housing;
   means for detachably securing an interventional element to a distal end of the drive member; and a plurality of structurally distinct interventional elements capable of attaching to said means for securing on the drive member, whereby the interventional elements may be attached and removed from the drive member while the means for detachably securing is extended distally of the open distal end of the cylindrical housing; and a terminal component detachably secured to the open distal end of the cylindrical housing; whereby the terminal component may be removed to allow the distal end of the drive member to be extended beyond the distal end of the housing, wherein an aperture is formed on a side of the housing and the structurally distinct interventional elements include a circular blade having a smooth edge and a circular blade having a serrated edge.

12. A catheter system comprising:
a flexible tube having proximal and distal ends;
a cylindrical housing secured to the distal end of the flexible tube, said housing having an open distal end and an aperture formed on a side thereof, wherein the open distal end is internally threaded and terminates in a constriction having a preselected diameter; and
a terminal component having proximal and distal ends, wherein (1) said proximal end is threaded to mate with the internal housing threads and is sufficiently large so that it cannot pass through the constriction, (2) said distal end is able to extend through the open end of the housing when the terminal component is threaded in place, and (3) said terminal component and housing aperture are sized so that the terminal component can pass through the aperture.

13. A catheter system as in claim 12, further comprising a plurality of structurally distinct interchangeable terminal components.

14. A catheter system as in claim 13, wherein the interchangeable terminal components are selected from the group consisting of an end piece having a fixed guide wire, an end piece having a central channel for receiving a movable guide wire, an end piece having an off-set channel for receiving a movable guide wire, an end piece having a rotatable tip, an end piece having a fixed hollow spring tip, and an end piece having a dilatation balloon.

15. A catheter system as in claim 12, further comprising:
a drive member extending within the flexible tube from its proximal end to the housing, said drive member being capable of both rotation and axial translation relative to said housing;
means for detachably securing an interventional element to a distal end of the drive member; and
a plurality of structurally distinct interventional elements capable of attaching to said means for securing on the drive member.

16. A method for using a catheter system to treat a patient, wherein said catheter system includes:
a flexible tube having proximal and distal ends;
a cylindrical housing secured to the distal end of the flexible tube and having an open, threaded distal end; and
a plurality of structurally distinct terminal components which are capable of interchangeably attaching to the distal end of the cylindrical housing;
said method comprising:
selecting a terminal component from said plurality of terminal components based on the patient's condition;
attaching said selected terminal component to the cylindrical housing; and
introducing the catheter to the vascular system of the patient;
wherein at least a distal region of the cylindrical housing and a proximal region of the terminal component are radiopaque so that said radiopaque regions appear to be continuous when the terminal component is properly joined to the housing but appear to be separated when the terminal component has loosened but not separated from the housing and the method further comprises observing the radiopaque regions while the catheter is within the patient'vascular system in order to determine if the radiopaque region on the terminal component is separating from the radiopaque region on the housing.

17. A method as in claim 16, further comprising:
removing the catheter from the patient;
replacing the terminal component with another terminal component; and
reintroducing the catheter to the patient.

18. A method as in claim 16, wherein the terminal components are selected from the group consisting of an end piece having a fixed guide wire, an end piece having a central channel for receiving a movable guide wire, an end piece having an off-set channel for receiving a movable guide wire, an end piece having a rotatable tip, an end piece having a fixed hollow spring tip, and an end piece having a dilatation balloon.

19. A method for using a catheter system to treat a region of stenosis within the vascular system of a patient, wherein said catheter system includes:
a flexible tube having proximal and distal ends;
a cylindrical housing secured to the distal end of the flexible tube and having an open distal end;
a drive member extending within the flexible tube from its proximal end to the housing; and
a plurality of structurally distinct interventional elements capable of attaching to a distal end of the drive member wherein at least a distal region of the housing is radiopaque and at least a proximal region of each terminal component is radiopaque so that said radiopaque regions appear to be continuous when the terminal component is properly joined to the housing but appear to be separated when the terminal component has loosened but not separated from the housing;
said method comprising:
selecting an interventional element from said plurality of interventional elements based on the patient's condition;
attaching said interventional element to the distal end of the drive member; and
introducing the catheter to the vascular system of the patient and positioning the housing near the region of stenosis; and
observing whether the radiopaque regions appear to separate.

20. A method as in claim 19, further comprising:
removing the catheter from the patient;
replacing the interventional element with another interventional element; and
reintroducing the catheter to the patient.

21. A method as in claim 19, wherein the interventional element is a circular cutting blade and the method further comprises rotating and axially translating the drive member in order to effect cutting of the atheroma.

22. A method as in claim 19, wherein the interventional element is an aspiration device and the method further comprises axially translating the drive member so that the aspiration device contacts the atheroma and applying a vacuum to the aspiration device to draw in atheroma.

* * * * *